United States Patent [19]

Taniguchi

[11] Patent Number: 4,622,033
[45] Date of Patent: Nov. 11, 1986

[54] AUTOMATED CATHETER CONSTRUCTION

[76] Inventor: Tokuso Taniguchi, 277 Kaiulani St., Hilo, Hi. 96720

[21] Appl. No.: 639,269

[22] Filed: Aug. 8, 1984

[51] Int. Cl.⁴ .......................................... A61M 25/00
[52] U.S. Cl. ................................... 604/172; 604/165; 604/265
[58] Field of Search ............... 604/172, 171, 173, 165, 604/170, 240, 242, 265, 268, 280, 283, 159

[56] References Cited

U.S. PATENT DOCUMENTS

| | | | |
|---|---|---|---|
| 3,515,137 | 6/1970 | Santomieri | 604/165 |
| 3,854,483 | 12/1974 | Powers | 604/172 |
| 3,861,395 | 1/1975 | Taniguchi | 604/172 |
| 3,898,993 | 8/1975 | Taniguchi | 604/172 |
| 3,967,728 | 7/1976 | Gordon et al. | 604/172 |
| 4,235,232 | 11/1980 | Spaven et al. | 604/171 |
| 4,269,310 | 5/1981 | Uson | 604/172 |
| 4,419,094 | 12/1983 | Patel | 604/180 |

Primary Examiner—Stephen C. Pellegrino
Assistant Examiner—Mark Rooney
Attorney, Agent, or Firm—Harvey B. Jacobson

[57] ABSTRACT

A catheter assembly for packaging in sterile condition within a protective removable envelope is provided. The catheter assembly includes a shield structure incorporating an elongated hollow body defining a bore therethrough. The body is separable into two halves and each half of the body has a portion of the shield structure supported therefrom. A catheter has its distal end slidingly telescoped into one end of the bore and a tubular lubricant reservoir is provided and includes a first open end and a second collapsible bulbous end. The open end is telescoped over the distal end of the catheter and into the corresponding end of the body bore. The reservoir has a frangible seal within its open end and telescoping engagement of the open end of the reservoir into the body bore functions to clamp the distal end of the catheter against withdrawal from the body bore. The proximal end of the catheter is contained within a sealed and readily openable tubular envelope and the envelope has one end thereof sealingly engaged with the separable portions of the shield. In addition, the envelope, adjacent its end remote from the shield sealingly receives therethrough the discharge neck of a collapsible fluid reservoir.

12 Claims, 9 Drawing Figures

AUTOMATED CATHETER CONSTRUCTION

BACKGROUND OF THE INVENTION

Various types of lubricatable catheters and catheters specifically designed for sterile packaging heretofore have been designed. Examples of such previously patented catheters may be found in U.S. Pat. Nos. 3,077,194, 3,154,080, 3,176,691, 3,275,001, 3,345,988, 3,444,860, 3,515,173, 3,556,294, 3,595,230, 3,566,874, 3,592,192, 3,605,752, 3,606,889, 3,672,376, 3,675,658, 3,677,244, 3,682,173, 3,683,298, 3,750,875, 3,776,915, 3,861,395, 3,898,933, 3,967,728, 4,062,363 and 4,140,127. Although these numerous prior types of catheters have been developed, a need still exists for a catheter construction which will lend itself more favorably to sterile packaging, ease in lubrication by lubricant also contained within the sterile packaging and ease of insertion by way of a tubular guide through which the catheter is advanced during insertion and which may be readily separated from about the catheter after insertion.

BRIEF DESCRIPTION OF THE INVENTION

The automated catheter assembly of the instant invention has been designed to simplify the catheterization of either the male urinary bladder or the female urinary bladder. The automated catheter assembly may utilize substantially any accepted rubber catheter or its equivalent and includes structure whereby the associated catheter may be lubricated in a sterile manner as it is placed in use and inserted into the female urethra or male penis without contamination of the rubber catheter during insertion. Also, the automated catheter assembly is provided with a support body having a bore formed therethrough and the associated catheter is advanced through the bore while one hand supports the body in alignment with the female urethra or the male penis. Still further, the catheter assembly includes structure for inflation of the catheter balloon and the aforementioned support body includes opposite side shield portions whereby adjacent portions of the patient's body are shielded against contact with the distal end of the catheter and body and the shield may be readily broken away from the proximal end of the catheter after the latter has been inserted.

The main object of this invention is to provide a catheter assembly designed to simplify the catheterization of male and female patients. Another object of this invention is to provide a catheter assembly wherein the catheter may be readily lubricated in a sterile state immediately prior to insertion of the distal end of the catheter.

Another important object of this invention is to provide for ease of inflation of the catheter balloon.

Still another object of this invention is to provide a catheter assembly including shield structure for shielding the distal end of the catheter from contact with parts of the body other than the urethra of the female patient and the penis of a male patient.

Another important object of this invention is to provide an automated catheter assembly in accordance with the preceding objects and which may be used in conjunction with a conventional catheter.

A final object of this invention to be specifically enumerated herein is to provide a catheter assembly in accordance with the preceding objects and which will conform to conventional forms of manufacture, be of simple construction and easy to use so as to provide a device that will be economically feasible, simple to use and relatively trouble free in operation.

These together with objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
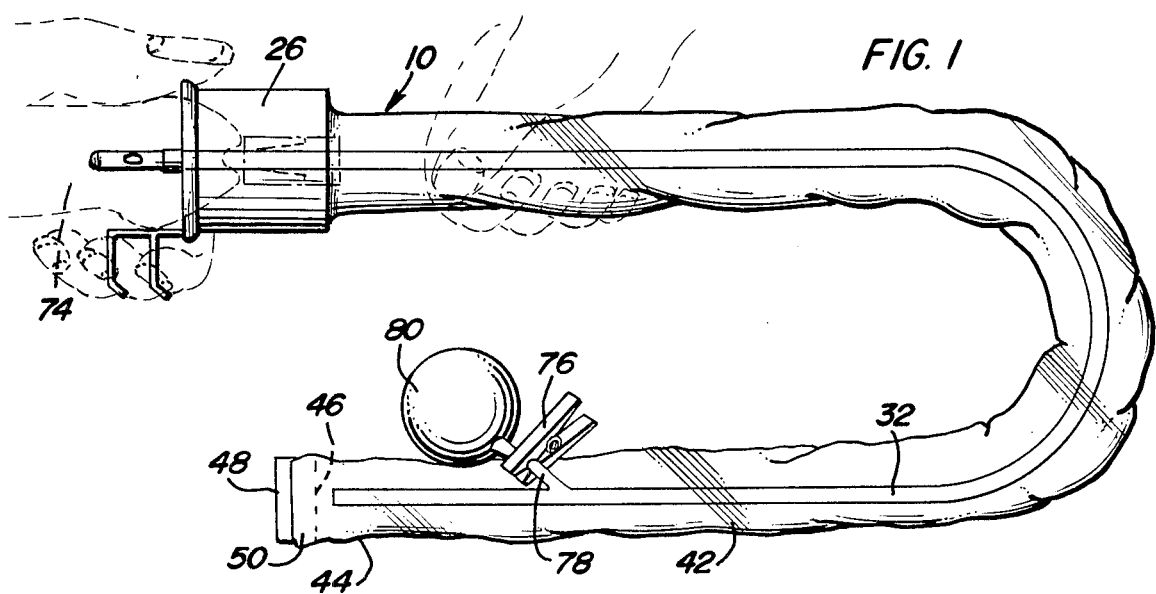
FIG. 1 is a side elevational view of a catheter assembly constructed in accordance with the present invention and adapted to be utilized in catheterizing a male patient.

Referring now more specifically to the drawings the numeral 10 generally designates a catheter assembly for utilization in conjunction with male catheterization. The catheter assembly 10 includes a generally cylindrical body 12 defining a longitudinal bore 14 formed therethrough. The body 12 includes a forward or distal end 16 and a rear or proximal end 18 inclusive of a generally circular end wall 20 having a central aperture 22 formed therein.

Formed integrally with the end 18 is a generally circular plate 24 and a generally cylindrical shield 26 which projects forwardly of the outer periphery of the plate 24. The plate 24 is centrally apertured and anchored relative to the body 12. However, the shield 26, plate 24 and body 12 are provided with vertically aligned slots 28 and 30 above and below the aperture 22. Frangible bridging portions 32 and 34 bridge the slot 30 closely beneath the lower portion of the body 12 and along the lower periphery of the shield 26.

A conventional catheter 32 has its balloon-equipped anterior end 34 telescoped forwardly through the aperture 22 and the body 12 and the interior of the body 12 includes peripherally spaced inclined fingers 36 which project forwardly and inwardly from the body 12 and closely embrace the catheter 32 at their inner ends. The body 12 also includes an apertured interior partition 38 spaced forward of the end wall 20 and defining a lubricant chamber 40 between the end wall 22 and the partition 38.

A flexible transparent tubular envelope 42 is provided and includes a forward end sealingly secured about and to the periphery of the plate 24 and a rear end 44 which is transversely sealed closed as at 46. The envelope 42 comprises a pair of flat strips superimposed upon each other and secured together along adjacent marginal edges in order to form the envelope. The rear ends of the strips are sealed together and illustrated as at 48 and 50 in FIG. 1 and may be pulled apart in order to separate the envelope 42 from about the catheter 32. In addition, the shield 26 may be separated by engaging the two shield halves disposed on opposite sides of the slots 28 and 30 by the lugs 52 provided thereon and pulling the two shield halves apart. In this manner, the two strips 48 and 50 of the envelope 42 may also be pulled apart inasmuch as each of the strips 48 and 50 is anchored relative to a corresponding shield half. The lower peripheral portion of the forward end of one of the shield halves includes a finger-engageable grip 54 projecting forwardly therefrom and including a pair of depending finger-engageable members 56 by which the shield 26 may be more readily handled, see FIG. 1.

Figure 2:
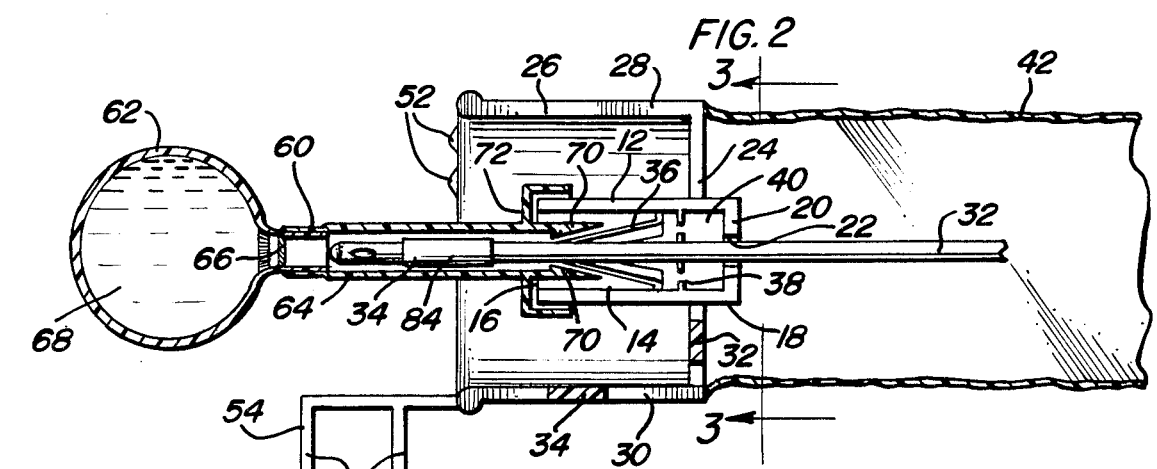
FIG. 2 is an enlarged fragmentary vertical sectional view of the anterior portion of the catheter construction.
Figure 4:
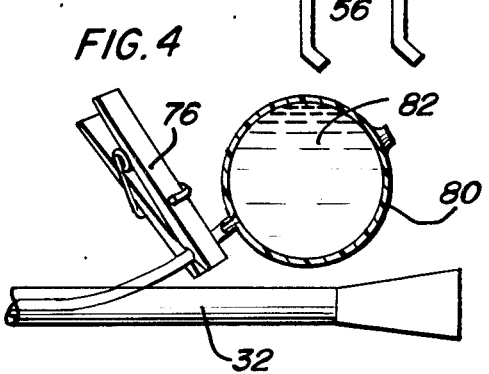
FIG. 4 is a fragmentary elevational view of the posterior end of the catheter with the protective envelope removed.
Figure 3:
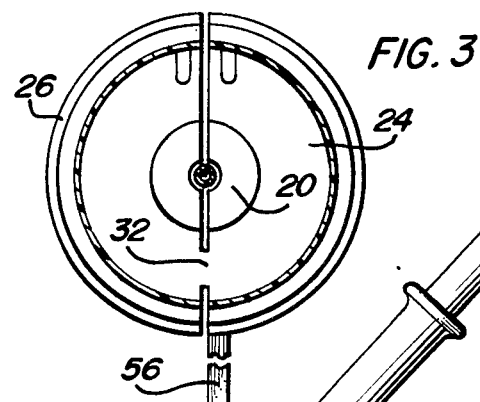
FIG. 3 is a transverse sectional view taken substantially upon the plane indicated by the section line 3—3 of FIG. 2.

With attention now invited more specifically to FIG. 2 of the drawings there may be seen a semi-liquid lubricant container 60 including a flexible and squeezable lubricant reservoir 62 and a lubricant outlet neck 64 which opens outwardly of the reservoir 62. The end of the outlet neck 64 adjacent the reservoir 62 has a pressure rupturable seal 66 secured across the interior thereof whereby the semi-liquid lubricant 68 within the reservoir 62 is prevented from drying. The end of the outlet neck 64 remote from the reservoir 62 includes interior wedge surfaces 70 engageable with the fingers 36 to inwardly deflect the adjacent forward ends thereof into lightly clamped engagement with the catheter 32. Thus, when the outlet neck 64 is inserted within the forward end of the body 12 to its limit of insertion defined by engagement of an abutment wall 72 carried by the outlet neck 64 with the forward end of the body 12 the fingers 36 lightly clampingly engage the catheter 32. Then, when the reservoir 62 is compressed between the fingers in order to break the seal 66 and express the lubricant 68 from the reservoir 62 and out through the outlet neck 64 the catheter 32 will not be projected rearwardly from the body 12. The forward end of the catheter 32 is fully lubricated and excess lubricant passes around the fingers and through the partition 38 and into the chamber 40. The lubricant within the chamber 40 serves to lubricate the catheter 32 disposed posteriorly of the shield 26 as the catheter 32 is inserted into the penis 74. After the anterior end of the catheter 32 has been positioned within the bladder the clamp 76 engaged with the outlet neck 78 of a pressurized liquid reservoir 80 is released and the liquid 82 within the reservoir 80 is allowed to flow from the reservoir 80 along the catheter in order to inflate the balloon portion 84 thereon. The clamp 76 is engaged with the outlet neck 78 through the envelope 42.

As may be seen from FIG. 1 of the drawings, the catheter 32 after the lubricant has been expressed from the reservoir 62, may be readily inserted into the penis 74 in a sanitary manner by guiding the catheter 32, through the envelope 42, forwardly through the body 12.

Figure 5:
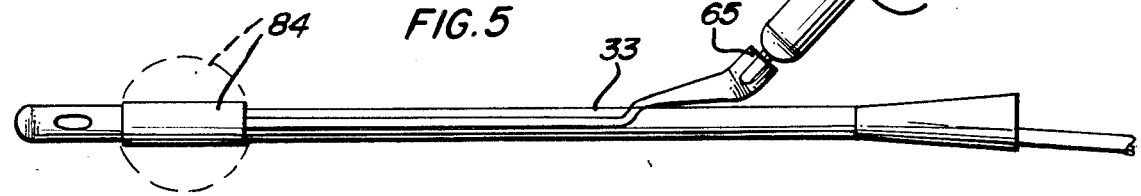
FIG. 5 is an elevational view of a modified form of catheter which may be used in conjunction with the shield and cover portion of the instant invention.
Figure 6:
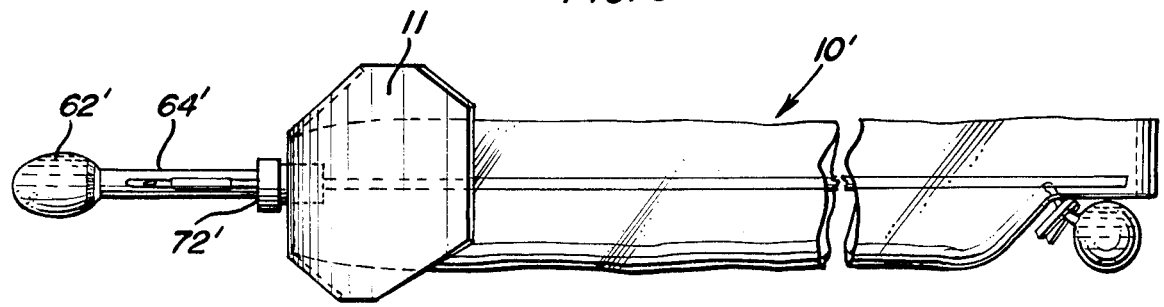
FIG. 6 is an elevational view of a catheter assembly constructed in accordance with the present invention and adapted to be utilized in catheterizing a female patient.
Figure 7:
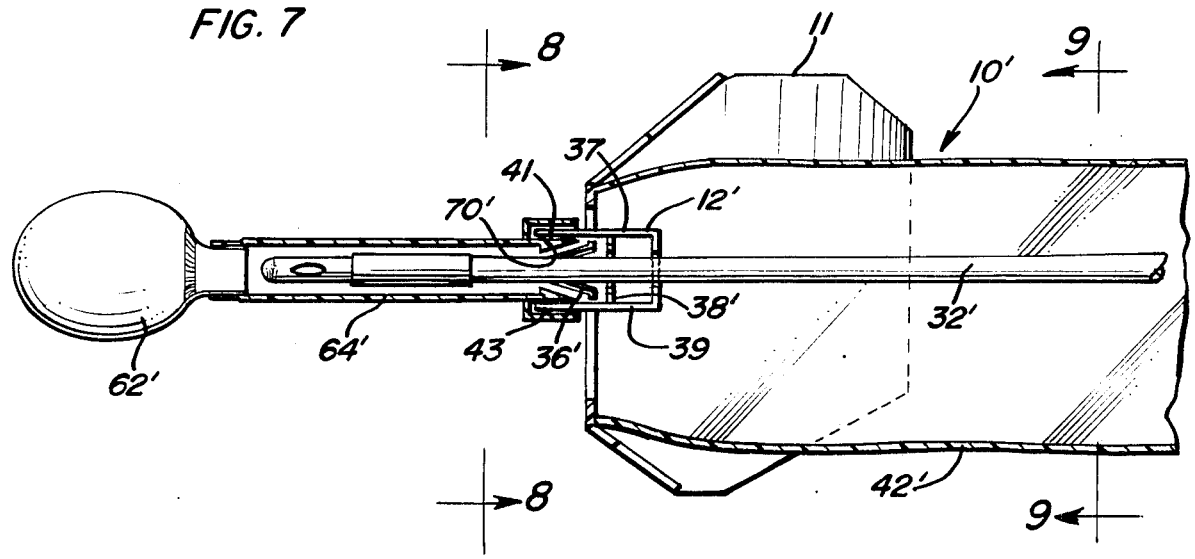
FIG. 7 is an enlarged fragmentary vertical sectional view of the anterior portion of the assembly illustrated in FIG. 6.
Figure 8:
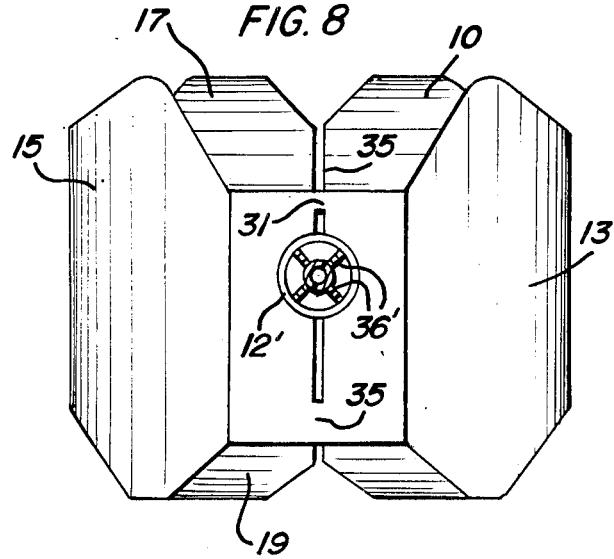
FIG. 8 is a transverse vertical sectional view taken substantially upon the plane indicated by the section line 8—8 of FIG. 7 and with the lubrication applying attachment removed.
Figure 9:
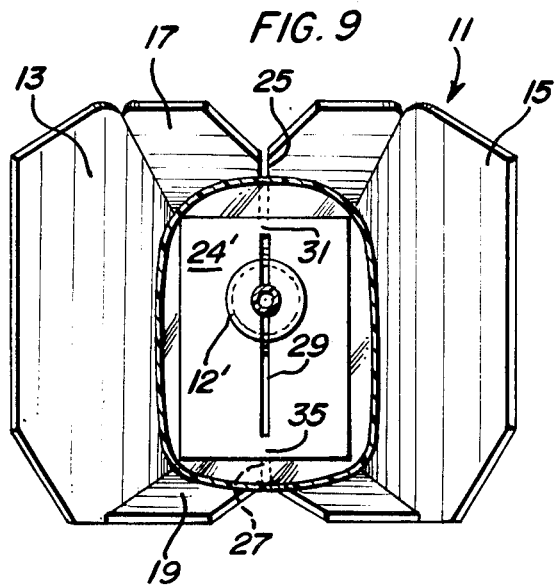
FIG. 9 is a transverse sectional view taken substantially upon the plane indicated by the section line 9—9 of FIG. 7.

If it is desired, a modified form of catheter 33 may be used, see FIG. 5, and the pressurized reservoir 80 of the catheter 32 may be replaced by a syringe 63 engageable through a plug 65 after the envelope 42 has been removed.

With attention now invited more specifically to FIGS. 6 through 9 of the drawings, there may be seen a modified form of catheter construction referred to in general by the reference numeral 10' and which is similar in many respects to the catheter 10 and therefore has the components thereof utilized on the catheter 10 referred to by prime reference numerals corresponding to the numerals used in conjunction with those similar components of the catheter construction 10.

The catheter construction 10' differs from the catheter construction 10 in that a shield referred to in general by the reference numeral 11 and incorporating rearwardly divergent opposite side panels 13 and 15 as well as rearwardly divergent upper and lower panels 17 and 19 is provided. The shield 11 is used in lieu of the shield 26 and includes a plate 24' corresponding to the plate 24 and from which a tubular body 12' corresponding to the body 12 is supported. However, the plates 17 and 19 are vertically slotted as at 25 and 27 and the plate 24' is vertically slotted as at 28 both above and below the body 12'. The plate 24' includes frangible connecting portions 31 and 35 and the body 12' includes vertically registered upper and lower slots 37 and 39 which terminate slightly rearward of the forward end of the body 12'. Thus, the body 12' includes connecting portions 41 and 43 which are frangible. In this manner, the shield 11 may have the two halves thereof broken apart by breaking the portions 31, 35, 41 and 43.

The catheter construction 10' includes an envelope 42' corresponding to the envelope 42 and a lubricant reservoir 62' incorporating an outlet neck 64' corresponding to the outlet neck 64 and also including wedges 70' engageable with fingers 36' corresponding to the fingers 36. Further, the body 12' includes a partition 38' corresponding to the partition 38.

The shield 11 is specifically adapted to be used in conjunction with a female patient and will of course prevent portions of the female patient closely adjacent the catheter construction 10' from coming in contact with the catheter 32' thereof.

As in the case with the male catheter construction 10, after the catheter 32' has been pushed sufficiently into the bladder and the catheter balloon has been inflated, the shield 11 may be separated by pulling the opposite sides of the shield apart and breaking the shield in the portions 31, 35, 41 and 43 thereof. Here again, the envelope 42' is constructed of a pair of opposite side strips which may be readily separated from the catheter along with the half sections of the shield, or the envelope 42' may have its two strips separated from the posterior end of the envelope 42'.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A catheter assembly including an elongated tubular body having opposite open ends, a catheter having its distal end slidingly and guidingly telescoped into one end of said body, a lubricant reservoir from which lubricant may be expressed and including a tubular outlet neck telescoped into and in axial alignment with the other end of said body and over said distal and of the catheter, said outlet neck and body including coacting means engaged with the outer surface of the catheter and operative to lightly clampingly engage said catheter to prevent longitudinal shifting of the latter relative to said body responsive to penetration of said outlet neck into said other end of said body with the clamping force being exerted solely by said outlet neck, whereby lubricant discharged from said outlet neck into said body and toward said one end thereof will not be effective to shift said catheter proximally in said body, said one end of said body including a centrally apertured end wall at said one end of said body and extending radially inwardly thereof loosely receiving said catheter therethrough, said body including an apertured partition therein centrally through which said catheter is slightly received, said apertured partition being disposed intermediate said end wall and said coacting means, the interior of said body between said partition and said end wall defining a lubricant chamber for lubricating said catheter proximally of said distal end during distal shifting of said catheter relative to said body during insertion of said distal end through the urethra and into the bladder.

2. The catheter assembly of claim 1 wherein said body includes a peripherally extending and outwardly projecting plate adjacent said one end of the body, the outer periphery of said plate including a tubular guide shield projecting toward and beyond said other end of said body.

3. The catheter assembly of claim 2 wherein said shield, plate and body are longitudinally slotted into two halves and said two halves are joined by breakable portions bridging between said two halves, whereby said two halves may be manually gripped and pulled apart.

4. The catheter assembly of claim 2 wherein the distal end of said tubular guide shield includes a laterally outwardly projecting finger-engageable portion.

5. The catheter assembly of claim 1, wherein said body includes a peripherally extending and outwardly projecting plate, supported intermediate the ends of said body, the outer periphery of said plate including opposite side distally and outwardly projecting flanges and upper and lower outwardly and distally inclined flanges.

6. The catheter assembly of claim 6 wherein said upper and lower flanges, said plate and body are longitudinally slotted and held together by frangible bridging portions enabling the shield comprising said opposite side flanges and said upper and lower flanges to be manually broken in half.

7. The catheter assembly of claim 6 including a tubular flexible envelope comprising opposite side strips releasably secured together along corresponding longitudinal edge portions, said envelope being telescoped over the proximal end of said catheter and having its forward end secured to said plate about the proximal end of said body, said strips of said envelope being separable from each other when said plate and body are broken apart and moved outwardly in relation to each other.

8. The catheter assembly of claim 3 including a tubular flexible envelope comprising opposite side strips releasably secured together along corresponding longitudinal edge portions, said envelope being telescoped over the proximal end of said catheter and having the forward ends of said side strips secured to the halves of said shield with the corresponding longitudinal edge portions aligned with the slots in the shield, said strips of said envelope being separable from each other when said shield is broken in half and the separated halves moved laterally away from each other.

9. The catheter assembly of claim 1 wherein said lubricant reservoir is provided with seal means to prevent lubricant in the reservoir from drying during storage, said seal means being rupturable by pressure when lubricant is expressed from said reservoir by subjecting the lubricant to pressure.

10. The catheter assembly of claim 1 wherein said coacting means includes a plurality of inclined fingers extending longitudinally and inwardly from said body with the free ends of the fingers received in the end of the outlet neck on the lubricant reservoir, said outlet neck including an inwardly facing, longitudinally extending wedge surface engaged with the outer surface of the fingers and deflecting them inwardly into clamping engagement with the catheter in response to longitudinal inward movement of the outlet neck in relation to the body.

11. A lubricating and guiding assembly for a catheter for use in inserting the catheter into a body orifice comprising a tubular body having a longitudinal bore extending therethrough adapted to receive a catheter therethrough, shield meas attached to the tubular body and projecting laterally thereof for engagement by the fingers of a person using the device to position the tubular body in alignment with the body orifice to facilitate alignment of and insertion of the catheter received through the tubular body into the body orifice, a lubricant reservoir including a squeezable bulb having a quantity of lubricant therein and a pressure rupturable seal preventing the lubricant from drying out during storage, said lubricant reservoir including a tubular outlet neck aligned with the tubular body and adapted to receive the end of the catheter when the catheter is positioned through the tubular body, said tubular body and shield means being constructed of two separable halves joined together by frangible connecting means, said tubular body including inwardly extending means movable inwardly for clamping engagement with a catheter received in the tubular body when the outlet neck is moved longitudinally into engagement with the inwardly extending means for deflecting the inwardly extending means inwardly for clamping engagement with the catheter without exerting any outward force on the tubular body and shield means thereby eliminating breakage of the frangible connecting means between the halves of the body and shield means while the outlet neck is engaged with the inwardly extending means and lubricant is being discharged into the interior of the tubular body so that discharge of the lubricant will not dislodge a catheter received in the tubular body and the lubricant will be applied to the catheter as it moves through the tubular body into a body orifice after the lubricant reservoir and outlet neck have been separated from the tubular body, said inwardly extending means on the tubular body including a plurality of deflecctable fingers each having one end rigid with the body and a free end extending longitudinally and inwardly of the tubular body with the inner end of the outlet neck including a wedging surface engaging the outlet surfaces of the fingers to deflect the fingers inwardly when the outlet neck is moved longitudinally inwadly in relation to the fingers.

12. The structure as defined in claim 11 together with a flexible protective envelope adapted to completely enclose the catheter with one end of the envelope being connected to the shield means and the envelope including longitudinal edge portions separably connected with the longitudinal edge portions being in alignment with the juncture between the two halves of the shield means and body for separation of the envelope when the two halves of the shield means and body are separated and moved apart.

* * * * *